United States Patent
Wong et al.

(10) Patent No.: US 9,259,961 B2
(45) Date of Patent: Feb. 16, 2016

(54) LARGE-AREA ULTRASOUND CONTACT IMAGING

(75) Inventors: Serena Han Ying Wong, Menlo Park, CA (US); Jeng Ping Lu, Fremont, CA (US); Raj B. Apte, Palo Alto, CA (US)

(73) Assignee: PALO ALTO RESEARCH CENTER INCORPORATED, Palo Alto, CA (US)

( * ) Notice: Subject to any disclaimer, the term of this patent is extended or adjusted under 35 U.S.C. 154(b) by 712 days.

(21) Appl. No.: 12/965,793

(22) Filed: Dec. 10, 2010

(65) Prior Publication Data

US 2012/0147698 A1 Jun. 14, 2012

(51) Int. Cl.
| | |
|---|---|
| G01S 15/00 | (2006.01) |
| A61B 8/00 | (2006.01) |
| B60B 1/02 | (2006.01) |
| G06K 9/00 | (2006.01) |
| G01S 7/56 | (2006.01) |
| A61B 8/08 | (2006.01) |
| A61B 5/117 | (2006.01) |

(52) U.S. Cl.
CPC .............. *B60B 1/02* (2013.01); *G06K 9/0002* (2013.01); *A61B 5/1172* (2013.01); *A61B 8/08* (2013.01); *G01S 7/56* (2013.01)

(58) Field of Classification Search
USPC .......................................................... 367/7
See application file for complete search history.

(56) References Cited

U.S. PATENT DOCUMENTS

| | | | | |
|---|---|---|---|---|
| 5,456,256 A | * | 10/1995 | Schneider et al. | 600/445 |
| 5,483,963 A | * | 1/1996 | Butler et al. | 600/437 |
| 6,552,841 B1 | * | 4/2003 | Lasser et al. | 359/305 |
| 7,400,750 B2 | | 7/2008 | Nam | |
| 7,739,912 B2 | | 6/2010 | Schneider et al. | |
| 8,201,739 B2 | | 6/2012 | Schneider et al. | |
| 8,601,876 B2 | | 12/2013 | Schneider et al. | |
| 2002/0049381 A1 | * | 4/2002 | Eck et al. | 600/447 |
| 2005/0094855 A1 | * | 5/2005 | Proano et al. | 382/124 |
| 2005/0105784 A1 | * | 5/2005 | Nam | 382/124 |
| 2006/0174717 A1 | * | 8/2006 | Ishikawa | 73/861.25 |
| 2007/0180916 A1 | * | 8/2007 | Tian et al. | 73/649 |
| 2007/0258628 A1 | * | 11/2007 | Schneider et al. | 382/124 |
| 2008/0219098 A1 | * | 9/2008 | Schneider et al. | 367/117 |
| 2008/0258580 A1 | * | 10/2008 | Schneider et al. | 310/334 |
| 2008/0303779 A1 | * | 12/2008 | Machida et al. | 345/107 |

(Continued)

FOREIGN PATENT DOCUMENTS

WO 2011112622 A1 9/2011

OTHER PUBLICATIONS

Bicz, Wieslaw, et al., "Ultrasonic Sensor for Fingerprints Recognition", SPIE, vol. 2634, pp. 104-111, 2004.

(Continued)

*Primary Examiner* — James Hulka
(74) *Attorney, Agent, or Firm* — Blakely Sokoloff Taylor & Zafman LLP

(57) ABSTRACT

An embodiment is a method and apparatus for ultrasonic contact imaging. A thin-film transistor (TFT) array is deposited on a substrate. A receiver having a plurality of receiver elements is deposited on the TFT array to receive a received signal. A transmitter adjacent to the receiver generates a transmit signal at an ultrasonic frequency. The transmit signal is reflected from a surface to produce a reflected signal. The received signal is a superposition of the transmit signal and the reflected signal as result of interference. The received signal is representative of differences in acoustic impedances across the surface.

25 Claims, 7 Drawing Sheets

(56) References Cited

U.S. PATENT DOCUMENTS

2009/0058714 A1* 3/2009 Vacanti .................. 342/120
2009/0150994 A1* 6/2009 Evans ..................... 726/20
2011/0215150 A1* 9/2011 Schneider et al. ........... 235/439
2011/0279662 A1 11/2011 Schneider et al.

OTHER PUBLICATIONS

Bicz, Wieslaw, et al., "Fingerprint Structure Imaging Based on an Ultrasonic Camera", vol. 27, No. 4, pp. 295-303, 1999.

Saijo, Yoshifumi, et al., "High Frequency Ultrasound Imaging of Surface and Subsurface Structures of Fingerprints", IEEE, pp. 2173-2176, Aug. 2008.

Kino, Gordon S., Prof., "Acoustic Waves: Devices, Imaging, and Analog Signal Processing", pp. 41-47, 1987.

Saijo, Yoshifumi, et al., "High Frequency Ultrasound Imaging of Surface and Subsurface Structures of Fingerprints", IEEE, ppp. 2173-2176, Aug. 2008.

* cited by examiner

LARGE-AREA ULTRASOUND CONTACT IMAGING

TECHNICAL FIELD

The presently disclosed embodiments are directed to the field of semiconductor devices, and more specifically, to ultrasonic imaging.

BACKGROUND

Incoherent C-mode ultrasound detectors have been used for high resolution surface and contact imaging in scanned single element devices, similar to acoustic microscopes, and also 2D arrays. However, all of these detectors use a pulse-echo methodology to collect reflectivity information from the surface of interest. The complexity of the electronics and acoustic structures needed to scale these devices to large areas becomes complex, impractical, or expensive.

Techniques for large-area ultrasound contact imaging have a number of disadvantages. High resolution, C-mode, contact/surface images may be acquired by scanning a highly focused ultrasound transducer over a surface, similar to an acoustic microscope. The focused transducer operates in pulse-echo mode, in which an ultrasound pulse or tone burst is transmitted to the surface and the received reflected response is peak detected at the appropriate time/range gate associated with the surface. Since scanning a single transducer is very time consuming, there has been development of large-area 2D arrays that collect a whole image plane synchronously. However, because the surface of interest is typically a large distance, greater than many wavelengths, away from the receiver face, large apertures are needed to maintain high resolution at the imaging surface. In the single element transducer system, this means that the scan step size and resolution at the focal point is often much smaller than the diameter of the single-element transducer. Thus, simply tiling single element transducers to produce a large-area array is not only difficult, but also will not provide the pixel density needed for large-area, 2D, ultrasound contact imaging.

U.S. Pat. No. 5,456,256 and U.S. Patent Application Number 2007/0258628 A1 describe two-dimensional (2D) array approaches that use dynamic focusing of smaller-sized elements. However, the electronics required to time delay and phase each element are complex and difficult to match over a large number of elements. This approach also requires the distribution of common reference signals, which is a challenge over a large area. Because of the complexity of these circuits, they prohibit the use of polysilicon thin film transistors (TFTs) and other low-cost, large-area electronics. Thus, the electronics requirements for this approach are prohibitively complex and expensive when scaled to large-areas.

Acoustic structures, such as lenses and waveguides, may be used to maintain high resolution for pulse-echo contact imaging with incoherent arrays. U.S. Pat. Nos. 5,483,963 and 6,552,841 describe large lenses used to focus ultrasound from the image plane onto an incoherent focal plane detector. In this approach, the resolution is limited by the aperture of the lens, which is not easily scalable to arbitrarily large areas. In addition, the lens structure requires large separations between the focal plane array, the lens, and the image plane; this limits the overall size of the final device.

U.S. Patent Application Numbers 2008/0258580 A1 and 2008/0219098 describe waveguide structures used to prevent ultrasound spreading to maintain resolution at the image plane. However, this structure suffers from difficulties in manufacturing and performance. To achieve the density and resolution needed, the acoustic waveguides often need to be spaced very close together (on the order of or smaller than a wavelength). Because the cores are spaced so closely together, the cladding layers are very thin and allow crosstalk between neighboring cores that degrades lateral resolution. In addition, fabricating the waveguide plates and aligning them with an array becomes increasingly difficult for large areas.

Pulse-echo structures and methods of ultrasound contact imaging are not scalable to large-area, incoherent devices capable of high-resolution, low-cost imaging.

SUMMARY

One disclosed feature of the embodiments is a technique for ultrasonic contact imaging. A thin-film transistor (TFT) array is deposited on a substrate. A receiver having a plurality of receiver elements is deposited on the TFT array to receive a received signal. A transmitter adjacent to the receiver generates a transmit signal at an ultrasonic frequency. The transmit signal is reflected from a surface to produce a reflected signal. The received signal is a superposition of the transmit signal and the reflected signal as result of interference. The received signal is representative of differences in acoustic impedances across the surface.

BRIEF DESCRIPTION OF THE DRAWINGS

Embodiments may best be understood by referring to the following description and accompanying drawings that are used to illustrate various embodiments. In the drawings.

DETAILED DESCRIPTION

One disclosed feature of the embodiments is a technique for ultrasonic contact imaging. A thin-film transistor (TFT) array is deposited on a substrate. A receiver having a plurality of receiver elements is deposited on the TFT array to receive a received signal. A transmitter adjacent to the receiver generates a transmit signal at an ultrasonic frequency. The transmit signal is reflected from a surface to produce a reflected signal. The surface is in contact with top layer of the device stack. The received signal is a superposition of the transmit signal and the reflected signal as result of interference. The thickness of the entire device stack is selected so that the received signal is representative of differences in acoustic impedances across the surface. These acoustic impedance differences result in different signal levels obtained at the receiver.

One disclosed feature of the embodiments may be described as a process which is usually depicted as a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a program, a procedure, a method of manufacturing or fabrication, etc. One embodiment may be described by a schematic drawing depicting a physical structure. It is understood that the schematic drawing illustrates the basic concept and may not be scaled or depict the structure in exact proportions.

One disclosed feature of the embodiments is a method and apparatus for incoherent ultrasound contact imaging with the large-area, low-cost advantages of the TFT technology. The technique may produce a high resolution, incoherent ultrasound contact imager using a quasi-continuous wave approach, instead of a pulse-echo approach. Two ultrasound waves are superimposed onto each other to image the reflectivity from a surface in contact with the imaging structure. Because the layers in this structure are thin to allow the two waves to interfere, the ultrasound may have a very short propagation distance, on the order of a wavelength. Thus, there is relatively little ultrasound spreading, which may enable the device to maintain high resolution without complex acoustic structures or focusing electronics. A simple range-gated peak detector may collect the reflectivity data, which enables the use of low-cost, large-area electronics, like polysilicon TFTs. Accordingly, one disclosed feature of the embodiments may be scalable to large-areas with minimal complexity and cost.

Figure 1:
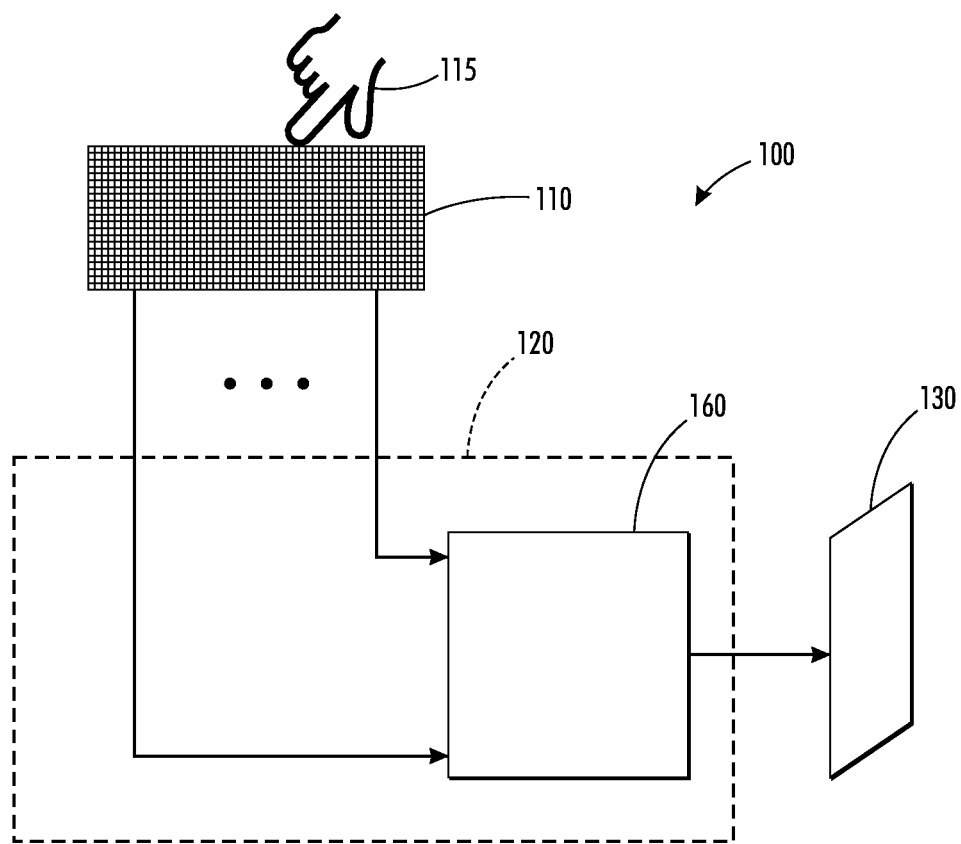
FIG. 1 is a diagram illustrating a system according to one embodiment.

FIG. 1 is a diagram illustrating a system 100 according to one embodiment. The system 100 includes an imaging structure 110, a processing circuit 120, and an image plane 130.

The imaging structure 110 is an ultrasonic contact imaging unit. It obtains an image of an object 115 using ultrasound operating in a quasi continuous wave (CW) mode. Operating in quasi CW mode allows much lower drive voltages be used. In pulse-echo mode, there is significant loss from diffraction and attenuation through materials over the large distances the ultrasound must travel. In the imaging structure 110, the travel distances are very short and there is interference of waveforms. For pulse-echo devices, transmitter voltages near 200 V peak-to-peak (pp) are needed to achieve a 100 mV pp signal on the receiver. In contrast, in the imaging unit 110, only 10 V pp may be needed on the transmitter to achieve approximately 100 mV pp signal on the receiver.

The imaging structure 110 may include a transmitter, a receiver, and a contact layer. The object 115 may be any object the image of which may be obtained by the imaging structure 110. The image is obtained when the object 115 makes a contact on the surface of the imaging structure 110. In general, the object 115 may have an impedance that is matched with the impedance of the top layer in the imaging structure 110. In one embodiment, the object 115 is a finger of a person whose fingerprint may be taken. The contact layer is the layer whose surface is in contact with the object 115. It is the top layer of the imaging structure 110. The imaging structure 110 transmits an ultrasound signal through the top layer. The transmit signal is reflected at the surface of the top layer to become a reflected signal. The reflected signal and the transmit signal are superimposed within the imaging structure and the combined signal is received by the receiver.

The processing circuit 120 is coupled to the imaging structure 110 to process the received signal to form an image. The image is then projected on the image plane 130.

Figure 2:
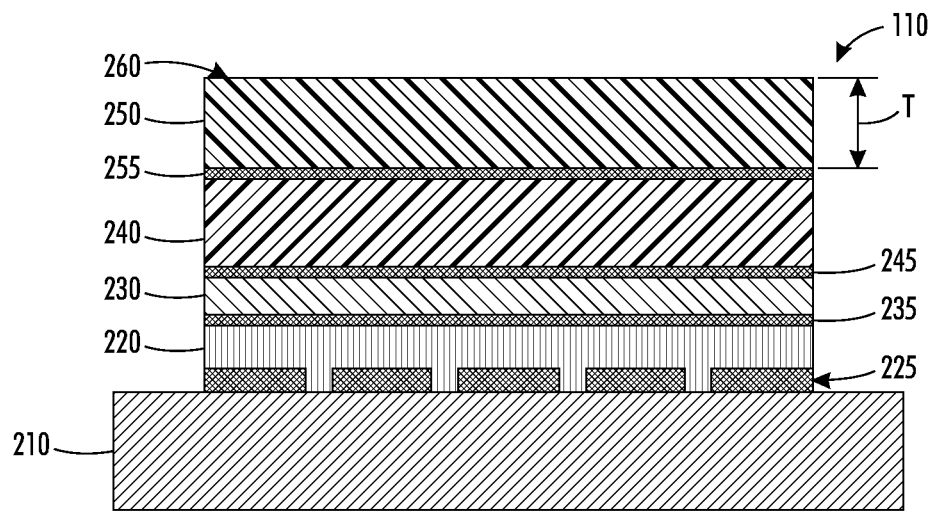
FIG. 2 is a diagram illustrating an ultrasonic contact imaging unit according to one embodiment.

FIG. 2 is a diagram illustrating the ultrasonic contact imaging unit 110 shown in FIG. 1 according to one embodiment. The imaging unit 110 includes a substrate 210, a thin-film transistor (TFT) array 225, a receiver 220, an insulator 230, a transmitter 240, and a contact layer 250. The imaging unit 110 may include more or less than the above elements. The acoustic stack has separate receiver and transmitter. Having separate transmit and receive transducers may be advantageous to eliminate the need for complicated electronics, such as high voltage transmit/receive switches, in each pixel. The high voltages needed on transmit may be separated both physically and electrically from the receivers. This may reduce the complexity of the pixel electronics by eliminating the high voltage transmit/receive switch common to most ultrasonic systems. This greatly simplifies the pixel electronics and enables the use of TFTs.

The substrate 210 may be any suitable substrate such as glass, quartz, plastic, stainless steel, or flexible polyimides. Steel may be advantageous because higher impedance materials may produce higher contrast ratio. The TFT array 225 is deposited on the substrate 210. It may be amorphous or polysilicon. It may include a plurality of individual TFT pixels and associated electrodes.

The receiver 220 is deposited on the TFT array 225 to receive a received signal. It may have a plurality of receiver elements corresponding to the plurality of TFT pixels. Each of the receiver elements may include a polymer receiver and a receiver circuit. The polymer receiver may be made of one of polyvinylidene fluoride (PVDF), polyvinylidene fluoride-trifluoroethylene (PVDF-TrFE), piezoelectric transducer (PZT), or electrostatic transducer. The receiver circuit may include a range-gated peak collector to collect the received signal to produce a pixel on the TFT array 225. On the receiver 220 is a conductive layer 235 which may contain the bias signal that is distributed across the plurality of receiver elements.

The insulator 230 may be any suitable dielectric or electrical insulator that separates the receiver 220 and the transmitter 240. The insulator 230 may be optional and may be completely eliminated. In this situation, the top electrode of the receiver 220 and the bottom electrode of the transmitter 240 may have to be both tied to ground to avoid shorts in the glue layer, which may happen over a large area.

The transmitter 240 is adjacent to the receiver 220 to generate a transmit signal to generate a transmit signal at an ultrasonic frequency. The transmit signal may be reflected from a surface 260 to produce a reflected signal. The transmitter 240 may have a ground layer 245 and a hot electrode layer 255. The transmitter 240 may be made of one of PVDF, PVDF-TrFE, PZT, or electrostatic transducer.

The contact layer 250 is deposited on the transmitter 240. It may have the layer surface 260 to receive contact from an object (e.g., object 115 shown in FIG. 1) having an object surface and a thickness such that the received signal is a superposition of the transmit signal and the reflected signal as result of signal interference. The received signal is representative of differences in acoustic impedances across the surface. These acoustic impedance differences result in different signal levels obtained at the receiver. When an object makes a contact on the layer surface 260, the received signal may be proportional to the reflectivity of the object surface at the layer surface 260 and therefore may characterize the structure of the object surface, thus providing an image of the object surface. The received signal may be subsequently processed to produce an image of the object surface.

The contact layer 250 may be made of one of mylar, epoxy, silicone, poly(methyl methacrylate) (PMMA), or polydimethylsiloxane (PDMS). The thickness T of the contact layer 250 may be less than a wavelength of the ultrasonic frequency. It may be chosen such that the transmit signal and the reflected signal are out of phase when there is no contact from the object 115 on the layer surface 260 resulting in the received signal having an approximately zero amplitude. Since the thickness T of this contact layer 250 is sub-wavelength, the propagation distance is short, which means that the imaging unit may provide good image resolution without the need for complex focusing electronics, lenses, or waveguide structures.

In addition to the above layers, additionally acoustic layers may be added to any place in the imaging structure 110 to improve electrical or acoustic properties. For instance, thicker layers of silver ink may be used as electrodes; this 6-micron ink may improve electrical conductivity, but a significant thickness may affect acoustic properties. Other layers added to the top of the device could also be used for acoustic matching purposes.

The thicknesses of the above layers in general may be modified so that the reflected and transmit signals are in phase or have any other phase relation to each other. For instance, modifying the layers of the structure so that the transmit and reflected signals are in-phase may produce contrast between objects of different impedance/reflectivity. In particular, the thickness of the stack may be selected such that the transmit and reflected signals are in-phase when there is no contact on the layer surface, resulting in the received signal being at the maximum. In general, the thickness of the entire device stack may be designed or selected so that the interference signal between the transmit signal and the reflected signal is representative of the differences in acoustic impedance across the surface. The acoustic impedance differences may result in different signal levels obtained at the receiver. In one embodiment, the effective acoustic length between the surface and the transmitter may be approximately an integer multiple of a quarter operating wavelength of the ultrasound.

Figure 3:
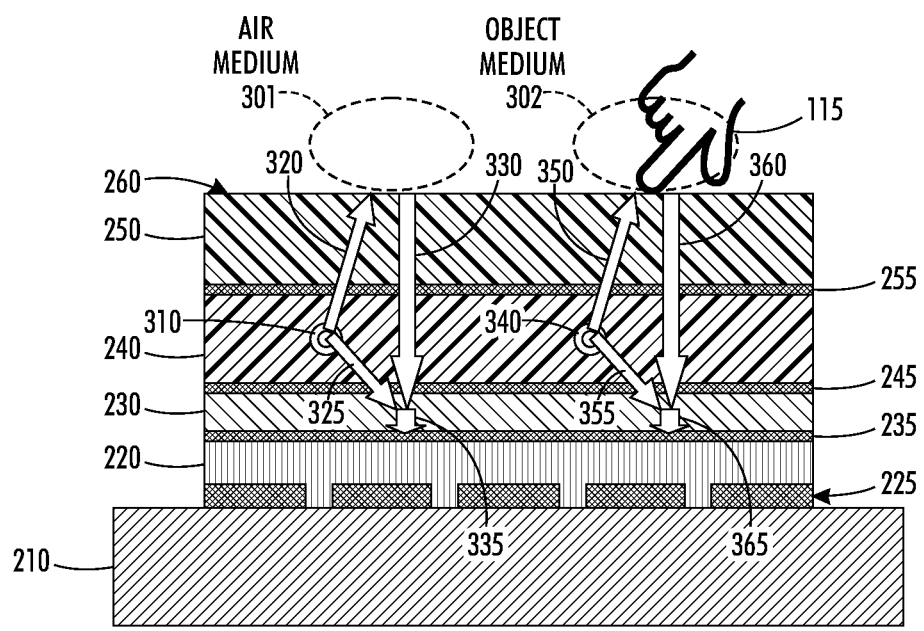
FIG. 3 is a diagram illustrating signals generated and received in the ultrasonic contact imaging unit according to one embodiment.

FIG. 3 is a diagram illustrating signals generated and received in the ultrasonic contact imaging unit 110 according to one embodiment. The imaging unit 110 forms an image by using the interference of the transmit signal and the reflected signal that enable reflectivity imaging from the surface 260 in contact with the contact layer 250. The transmitter 240 generates transmit signals 320 and 325 at point 310. In general, the transmit signals 320 and 325 are the same.

The transmit signal 320 is reflected at location 301 on the layer surface 260 to provide a reflected signal 330. The location 301 is where there is no object contact and air is the medium at the surface. Since air is at the surface, the reflection coefficient is nearly 100%. The thickness T of the contact layer 250 is chosen so that the transmit signal 320 (or 325) and the reflected signal 330 are 180-degree out of phase. The transmit signal 325 and the reflected signal 330 are superimposed due to signal interferences in the transmitter 240 to form a received signal 335 which is received by the receiver 220. Since they are 180-degree out of phase, or complementary to each other, their combined signal, or the received signal 335, may be approximately zero. In other words, when there is no object at the contact layer, the pixel is dark representing nothing or only air.

The transmitter 240 generates transmit signals 350 and 355 at point 340. In general, the transmit signals 350 and 355 are the same. Suppose the object 115 makes contact at location 302 on the layer surface 260 of the contact layer 250. The transmit signal 350 reflects at location 302 on the layer surface 260 to provide a reflected signal 360. The transmit signal 355 and the reflected signal 360 are superimposed due to signal interferences in the transmitter 240 to form a received signal 365 which is received by the receiver 220. Since the object 115 is now at the surface instead of air, the reflection coefficient is no longer 100%. Therefore, part of the transmit signal 350 is transmitted through the object 115 and part of it is reflected to become the reflected signal 360. The reflected signal 360 therefore is no longer 180-degree out of phase relative to the transmit signal 355. Accordingly, they do not completely cancel each other out. The received signal 365 therefore has non-zero magnitude. The value of the magnitude is proportional to the reflectivity at the layer surface 260 which is a function of the object surface. In other words, the received signal 365 is representative of differences in acoustic impedances across the surface.

Figure 4:
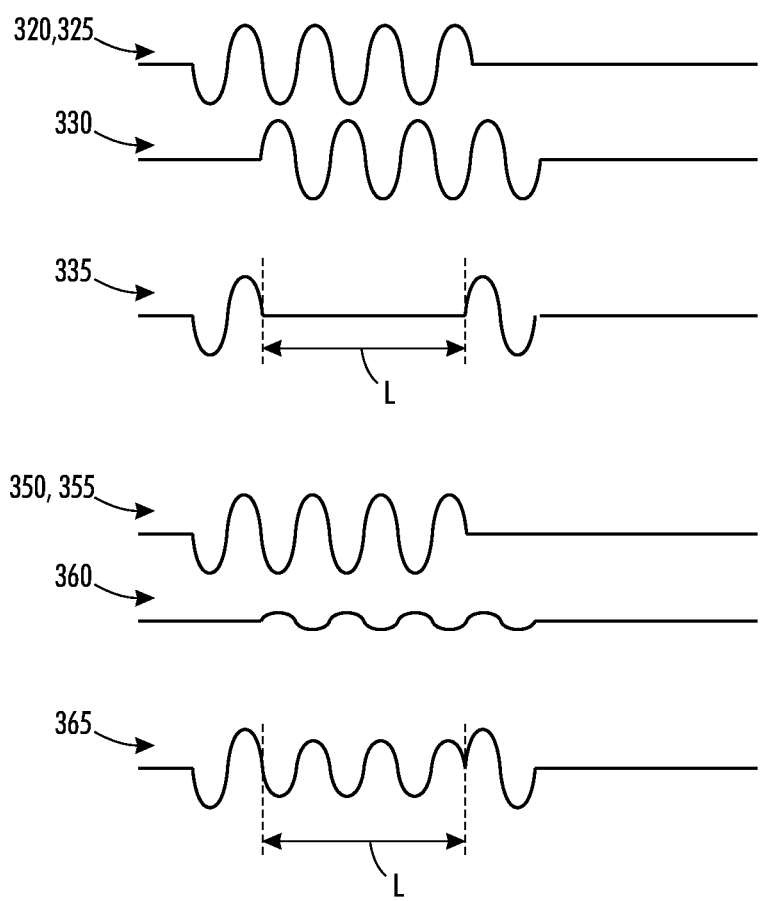
FIG. 4 is a diagram illustrating superposition of transmit signals and reflected signals according to one embodiment.

FIG. 4 is a diagram illustrating superposition of transmit signals and reflected signals according to one embodiment. The signals 320 and 325 represent the transmit signals generated by the transmitter 240. The signal 330 is the reflected signal when air is at the surface. It is 180-degree out of phase with respect to the signal 325. The signal 335 is the received signal which is the superposition of the signals 325 and 330. The signals 325 and 330 cancel each other out in the interval L. Accordingly, if the signal 335 is integrated over the integration period coincident with the interval L, its value becomes approximately zero.

The signals 350 and 355 represent the transmit signals generated by the transmitter 240. The signal 360 is the reflected signal when the object is at the surface. It is not out of phase with respect to the signal 355. The signal 365 is the received signal which is the superposition of the signals 355 and 350. The signals 355 and 350 do not cancel each other out in the interval L. Accordingly, if the signal 365 is integrated over the integration period coincident with the interval L, its value becomes non-zero and is proportional to the reflectivity at the surface and is therefore representative of differences in acoustic impedances across the surface.

Figure 5:
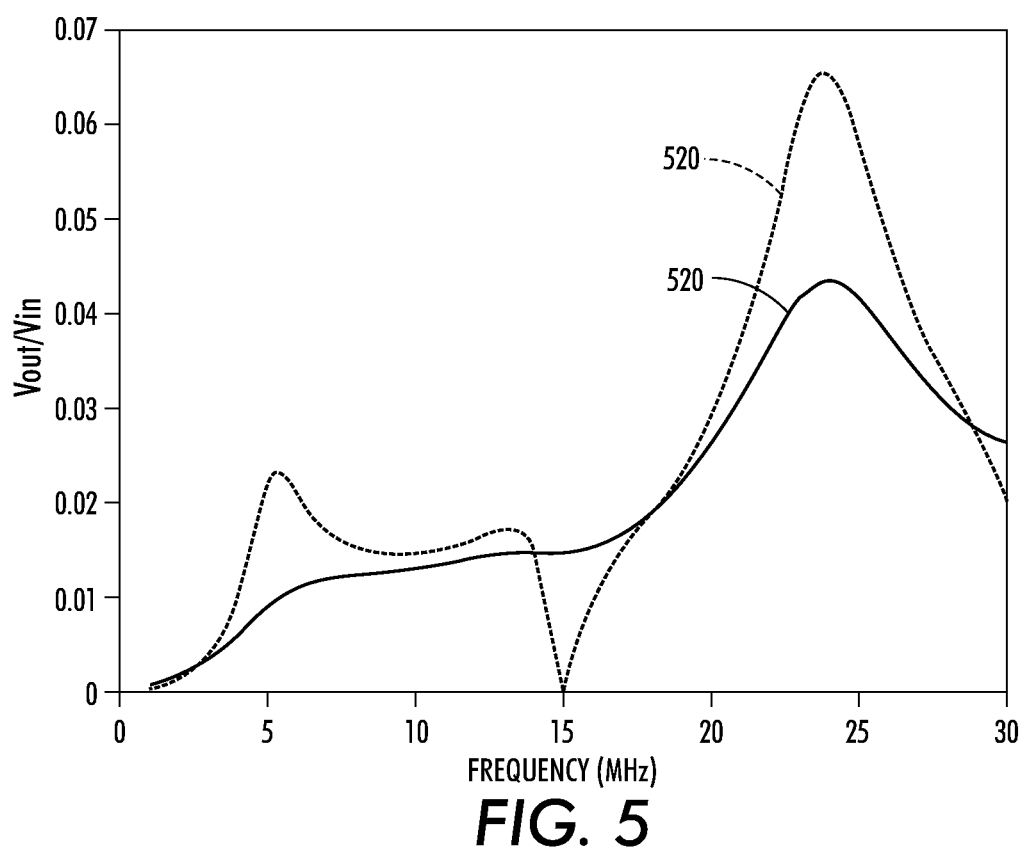
FIG. 5 is a diagram illustrating a frequency analysis of response according to one embodiment.

FIG. 5 is a diagram illustrating a frequency analysis of response according to one embodiment. A simulation has been carried out to verify the performance of the imaging unit 110. The simulation uses the continuous wave, transmission model for piezoelectric transducers. The imaging unit is simulated to have the following parameters: the ultrasonic frequency is 15 MHz, the receiver is a 12-micron PVDF-trFE, the transmitter is 12-micron PVDF, and the insulator is a 28-micron mylar. For this structure, the contact layer is a 65-micron mylar. The thickness of 65 microns is selected in order to completely cancel out the reflected signal.

The frequency response shows the ratio $V_{out}/V_{in}$ as function of frequency. Curve 510 corresponds to air at the surface and curve 52 corresponds to a finger t the surface. At 15 MHz, the frequency response shows a value of zero for air and non-zero value for finger. At this frequency, the contrast ratio is approximately 50 between fingerprint ridges and valleys (for air gaps).

Figure 6:
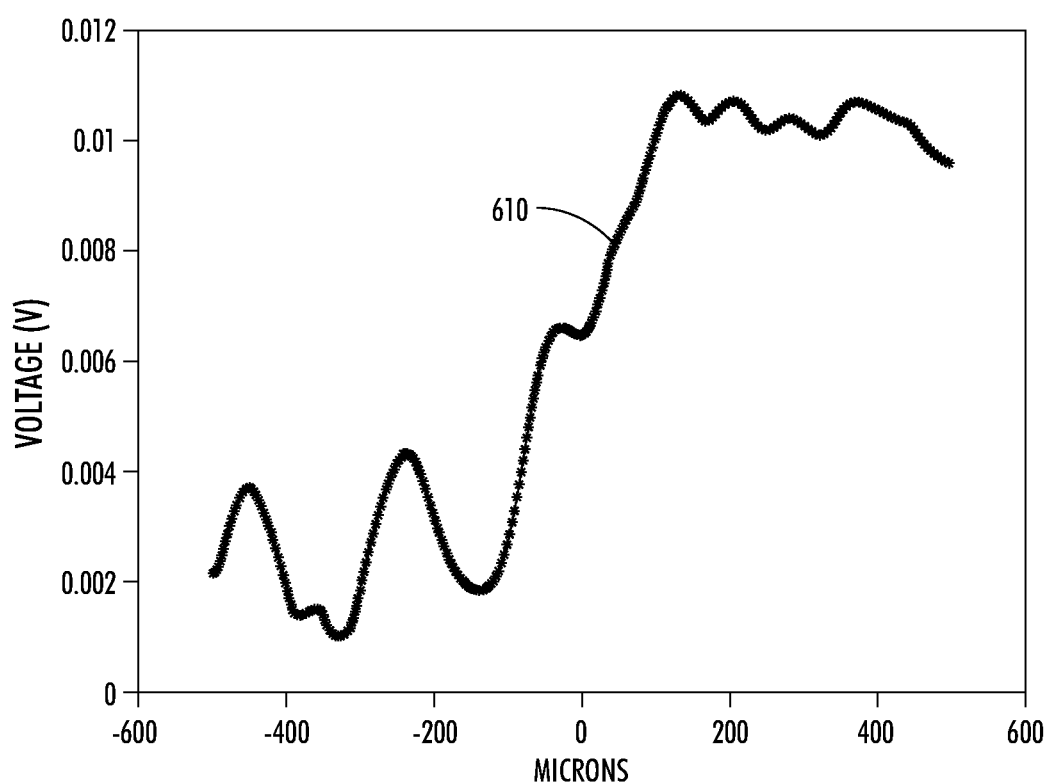
FIG. 6 is a diagram illustrating voltage at the receiver as function of distance according to one embodiment.

FIG. 6 is a diagram illustrating voltage at the receiver as function of distance according to one embodiment. Curve 610 represents the voltage at the receiver as function of the distance on the surface of the contact layer. At zero micron, there is a step transition from an air load on the surface of the contact layer to a finger load. The transition distance of approximately 200 micron indicates that the image resolution of the imaging unit is about 200 micron.

Figure 7:
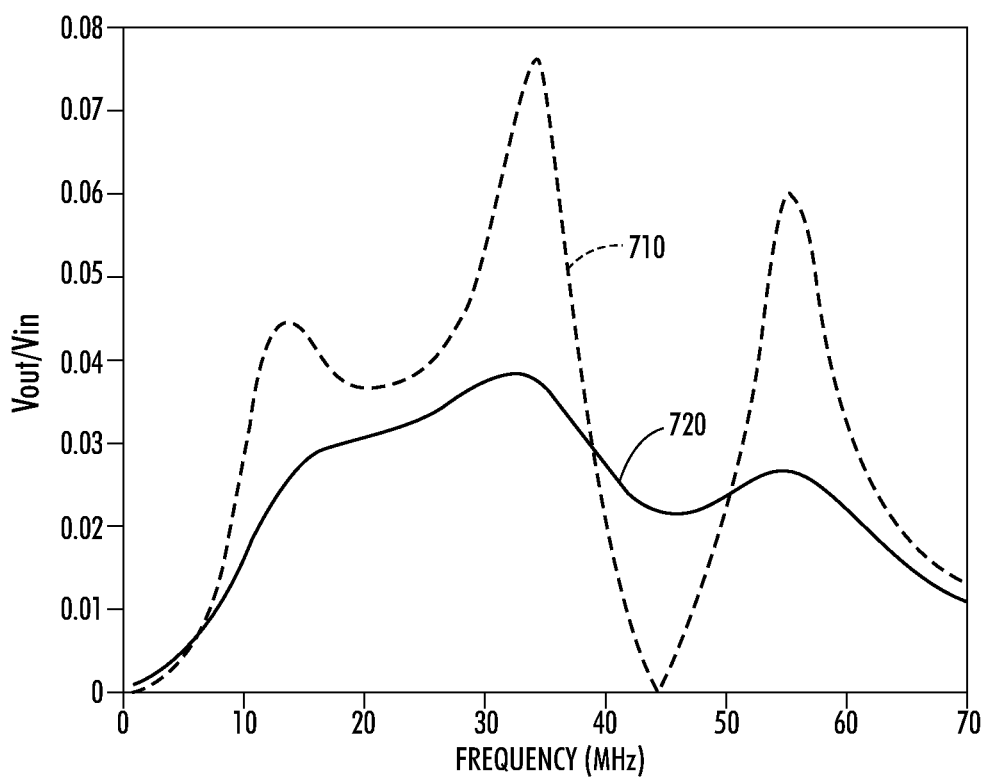
FIG. 7 is a diagram illustrating trade-off between frequency and contrast ratio according to one embodiment.

FIG. 7 is a diagram illustrating trade-off between frequency and contrast ratio according to one embodiment. By analyzing the frequency response, a trade-off between operating frequency and contrast ratio may be made. The contrast ratio may be proportional to the ratio between the responses at an operating frequency between the air load (e.g., when no contact) and the object load (e.g., when the object makes contact). Curve 710 corresponds to the air load. Curve 720 corresponds to the finger load.

At approximately 35 MHz where the response for both curves 710 and 720 are at peaks, the signals are larger, but the contrast ratio is only about 2. This frequency may be preferred when the electronic circuits may be noisy because the signal strength is high.

At approximately 43 MHz, curve 710 is at null while curve 720 is at some significant value. Accordingly, the contrast ration is an order of magnitude better than at 35 MHz.

Figure 8:
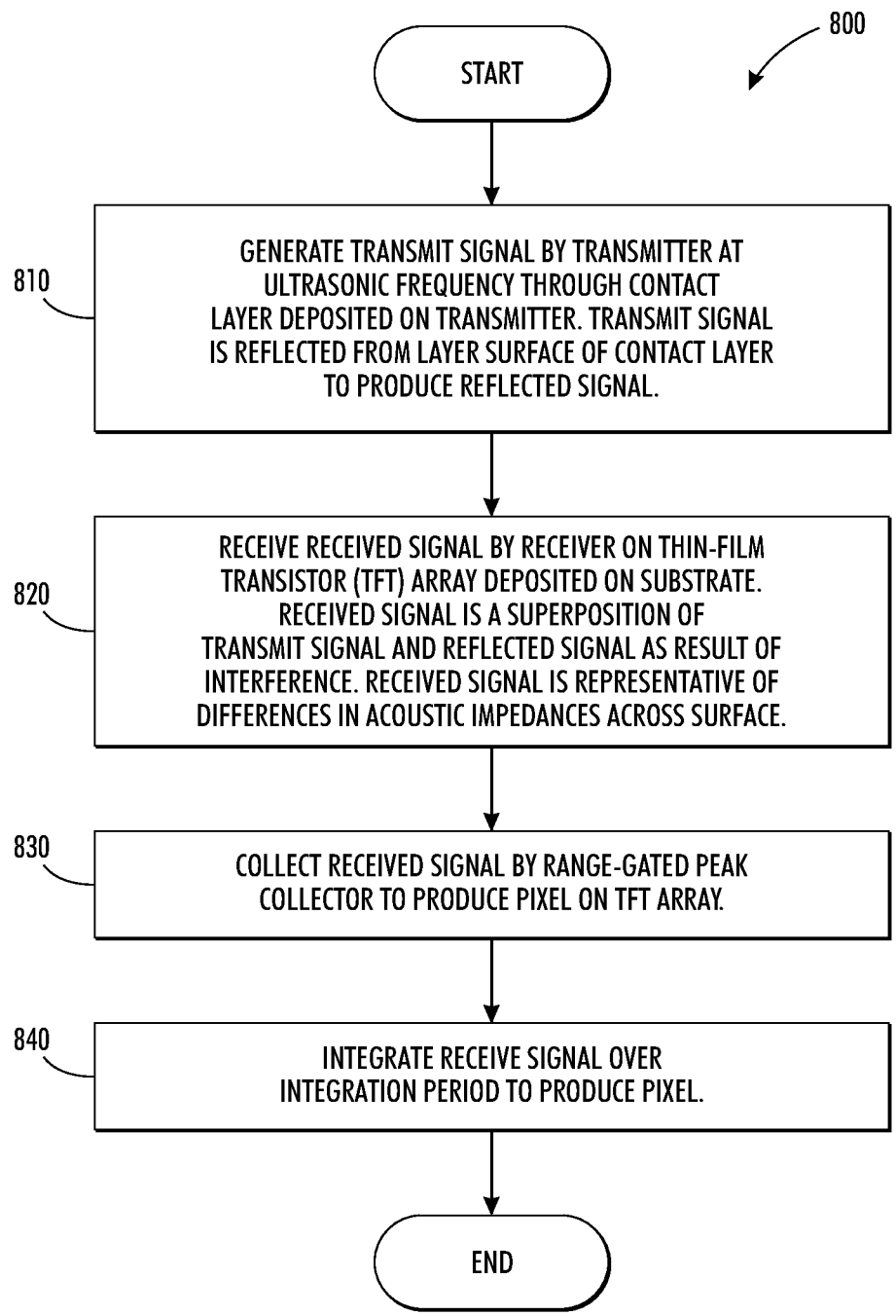
FIG. 8 is a flowchart illustrating a process to perform ultrasonic contact imaging according to one embodiment.

FIG. 8 is a flowchart illustrating a process 800 to perform ultrasonic contact imaging according to one embodiment.

Upon START, the process 800 generates a transmit signal by a transmitter at an ultrasonic frequency through a contact layer deposited on the transmitter (Block 810). The transmit signal is reflected from a layer surface of the contact layer to produce a reflected signal. Next, the process 800 receives a received signal by a receiver on a thin-film transistor (TFT) array deposited on a substrate (Block 820). The received signal is a superposition of the transmit signal and the reflected signal as result of interference. The received signal is representative of differences in acoustic impedances across the surface.

Then, the process 800 collects the received signal by a range-gated peak collector to produce a pixel on the TFT array (Block 830). Next, the process 800 integrates the receive signal over an integration period to produce the pixel (Block 840). The process 800 is then terminated.

It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. An apparatus comprising:
 a thin-film transistor (TFT) array deposited on a substrate;
 a receiver having a plurality of receiver elements deposited on the TFT array to receive a received signal;
 a transmitter adjacent to the receiver to generate a transmit signal at an ultrasonic frequency, the transmit signal being reflected from a surface to produce a reflected signal; and
 a contact layer deposited on the transmitter having the surface and a thickness such that the received signal is a superposition of the transmit signal and the reflected signal as result of interference, the received signal representative of differences in acoustic impedances across the surface.

2. The apparatus of claim 1 wherein each of the plurality of receiver elements comprises:
 a range-gated peak collector to collect the received signal to produce a pixel on the TFT array.

3. The apparatus of claim 1 wherein the transmitter generates the transmit signal in a quasi continuous wave (CW) mode.

4. The apparatus of claim 1 wherein the thickness of the contact layer is less than a wavelength of the ultrasonic frequency.

5. The apparatus of claim 1 further comprising:
 an insulator deposited between the receiver and the transmitter.

6. The apparatus of claim 5 wherein the insulator is made of one of mylar, epoxy, silicone, poly(methyl methacrylate) (PMMA), or polydimethylsiloxane (PDMS).

7. The apparatus of claim 1 wherein the substrate is glass, quartz, plastic, or steel.

8. The apparatus of claim 1 wherein the contact layer is made of one of mylar, epoxy, silicone, poly(methyl methacrylate) (PMMA), or polydimethylsiloxane (PDMS).

9. The apparatus of claim 1 wherein one of the receiver and the transmitter is made of one of polyvinylidene fluoride (PVDF), polyvinylidene fluoride-trifluoroethylene (PVDF-TrFE), piezoelectric transducer (PZT), or electrostatic transducer.

10. The apparatus of claim 1 wherein the thickness is chosen such that the transmit signal and the reflected signal are out of phase when there is no contact from an object on the surface, resulting in the received signal having an approximately zero amplitude.

11. The apparatus of claim 1 wherein the thickness is chosen such that the transmit signal and the reflected signal are in-phase when there is no contact from an object on the surface, resulting in the received signal having an approximately maximum amplitude.

12. The apparatus of claim 1 wherein an effective acoustic length between the surface and the transmitter is approximately an integer multiple of a quarter of operating wavelength.

13. A method comprising:
 generating a transmit signal by a transmitter at an ultrasonic frequency through a contact layer deposited on the transmitter, the transmit signal being reflected from a surface of the contact layer to produce a reflected signal; and
 receiving a received signal by a receiver on a thin-film transistor (TFT) array deposited on a substrate, the received signal being a superposition of the transmit signal and the reflected signal as result of interference, the received signal representative differences in acoustic impedances across the surface.

14. The method of claim 13 further comprising:
 collecting the received signal by a range-gated peak collector to produce a pixel on the TFT array.

15. The method of claim 13 wherein generating comprises generating the transmit signal in a quasi continuous wave (CW) mode.

16. The method of claim 13 wherein the contact layer has a thickness less than a wavelength of the ultrasonic frequency.

17. The method of claim 13 wherein the thickness is chosen such that the transmit signal and the reflected signal are out of phase when there is no contact from the object on the layer surface, resulting in the received signal having an approximately zero amplitude.

18. The method of claim 13 wherein the thickness is chosen such that the transmit signal and the reflected signal are in-phase when there is no contact from the object on the layer surface, resulting in the received signal having an approximately maximum amplitude.

19. The method of claim 13 further comprising:
 insulating the transmitter from the receiver by an insulator deposited between the receiver and the transmitter.

20. The method of claim 19 wherein the insulator is made of one of mylar, epoxy, silicone, poly(methyl methacrylate) (PMMA), or polydimethylsiloxane (PDMS).

21. The method of claim 13 wherein the substrate is glass, quartz, plastic, or steel.

22. The method of claim 13 wherein the contact layer is made of one of mylar, epoxy, silicone, poly(methyl methacrylate) (PMMA), or polydimethylsiloxane (PDMS).

23. The method of claim 13 wherein one of the receiver and the transmitter is made of one of polyvinylidene fluoride (PVDF), polyvinylidene fluoride-trifluoroethylene (PVDF-TrFE), piezoelectric transducer (PZT), or electrostatic transducer.

24. The method of claim 13 wherein an effective acoustic length between the surface and the transmitter is approximately an integer multiple of a quarter of operating wavelength.

25. A system comprising:
an imaging structure comprising:
- a thin-film transistor (TFT) array deposited on a substrate,
- a receiver having a plurality of receiver elements deposited on the TFT array to receive a received signal,
- a transmitter on the receiver to generate a transmit signal at an ultrasonic frequency, the transmit signal being reflected from a surface to produce a reflected signal, and
- a contact layer deposited on the transmitter having the surface and a thickness such that the received signal is a superposition of the transmit signal and the reflected signal as result of interference, the received signal representative of differences in acoustic impedances across the surface; and a processing circuit coupled to the imaging structure to process the received signal to form an image.

* * * * *